(12) United States Patent
Niven et al.

(10) Patent No.: US 6,834,959 B2
(45) Date of Patent: Dec. 28, 2004

(54) SPIDER-WEB PLACIDO PATTERN

(75) Inventors: Gregg D. Niven, Kaysville, UT (US); Joseph R. Bentley, West Jordan, UT (US); Barry T. Egan, Salt Lake City, UT (US); Lloyd Caldwell, Salt Lake City, UT (US); Lloyd Allred, Bountiful, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/261,539

(22) Filed: Sep. 30, 2002

(65) Prior Publication Data

US 2004/0061833 A1 Apr. 1, 2004

(51) Int. Cl.[7] .................................................. A61B 3/10
(52) U.S. Cl. ...................................................... 351/212
(58) Field of Search ................................ 351/205–212, 351/221, 246

(56) References Cited

U.S. PATENT DOCUMENTS

| 3,804,528 | A |   | 4/1974  | Kilmer et al. ............... 356/165 |
| 5,500,697 | A | * | 3/1996  | Fujieda ........................ 351/212 |
| 5,841,511 | A | * | 11/1998 | D'Souza et al. ............. 351/212 |
| 5,864,383 | A |   | 1/1999  | Turner et al. ................ 351/212 |
| 6,213,605 | B1 |  | 4/2001  | D'Souza et al. ............. 351/212 |
| 6,447,119 | B1 |  | 9/2002  | Stewart et al. .............. 351/212 |

* cited by examiner

*Primary Examiner*—George Manuel
(74) *Attorney, Agent, or Firm*—Michael L. Smith

(57) ABSTRACT

A placido pattern 10 for use in obtaining a topography of an eye, includes a series of spaced arcuate segments 12 centered about a central point 14 and a series of spaced radial lines 16 emanating from the central point 14. Each pair of adjacent radial lines 16 defines a boundary of a portion of the arcuate segments 12.

5 Claims, 2 Drawing Sheets

SPIDER-WEB PLACIDO PATTERN

BACKGROUND OF THE INVENTION

1. Field of the Invention

The present invention relates to a novel placido pattern. More specifically, the novel placido pattern of the present invention allows more topographical data to be gathered from the cornea than traditional block raster or concentric ring patterns presently used on other corneal topography systems.

2. Description of Related Art

The concentric ring pattern developed by Placido in the 19th century was developed on the premise that concentric ring patterns that are reflected from a human cornea would distort based upon the anterior shape of that cornea. In the case of radical change of curvature of the cornea, such as a smaller radius or more curvature, the rings would appear to be further apart. For areas that are larger in radius, the rings would appear to be closer together. For a perfectly spherical cornea, the rings would remain concentric and evenly spaced. The difficulty with Placido's hand held method is that the rings are hard to see due to lighting conditions and without a method of capturing the ring pattern, no review of the rings could take place.

Within the last twenty years or so, it has been found that if a recording device, such as a camera, captures these images, the captured images can be compared to an image from the reflection off of a close to perfect sphere. The differences between the two images then indicate how much the curvature of the anterior surface of the eye being tested has changed from a perfect sphere.

In addition, a mathematical relationship of elevation defined by curvature data has been developed, allowing a comparison of curvature to elevation. This means that if an image of a known radius sphere is captured and compared to an image of an unknown radius image, the elevation of the unknown surface can be calculated based upon the changes in curvature as indicated by the deviation of the rings from a perfectly circular pattern if the surface is irregular or by spacing if the surface is spherical.

The drawback to the above methodology is that for one point on an irregular cornea, the reflected rays can come from several locations on the pattern. Therefore, it is difficult to differentiate between points when the only reference circles. This becomes an issue when it is difficult to know where on a circular pattern a ray of light emanates from. This is commonly referred to as the twist angle. One attempt to deal with this problem resulted in the development of a pattern of alternating light and dark blocks arranged in a circular pattern which is disclosed in U.S. Pat. Nos. 5,841, 511 and 6,213,605 to D'Souza, et al. This block pattern allows a review of the captured image vertices or corners of each block to be located and to be compared with a known good image. The vertices can be systematically located which allows one to determine which rays create which points on the image captured by the camera. In addition, an array of dark and light blocks provides better data than only concentric circles as the points of data can be located in an array of blocks because more data points can be verified than on a simple circular pattern.

It is also known to use a grid pattern for obtaining topographical data of a cornea, such as disclosed in U.S. Pat. No. 5,864,383 to Turner, et al. One problem with the use of a simple grid is that it can become difficult identifying which grid data points go with which grid intersecting lines because an essentially square pattern is being overlayed onto a spherical object. The typical method of analysis requires the center of the image to be located first. This becomes the central reference axis. This usually is aligned with the optical axis, due to the method of patient fixation. Next, each concentric ring of the pattern is located and mapped on the image. This systematic progression is more easily done on concentric type patters than with simple raster patters. When only raster grid patters are used, it becomes more difficult to systematically locate points to ensure that references to the center axis and surface points are maintained.

Therefore, it would be advantageous to have a pattern that can accommodate the twist angle problem while being easily accommodated by the software algorithms of a topographical system.

DETAILED DESCRIPTION OF THE PREFERRED EMBODIMENT

Figure 1:
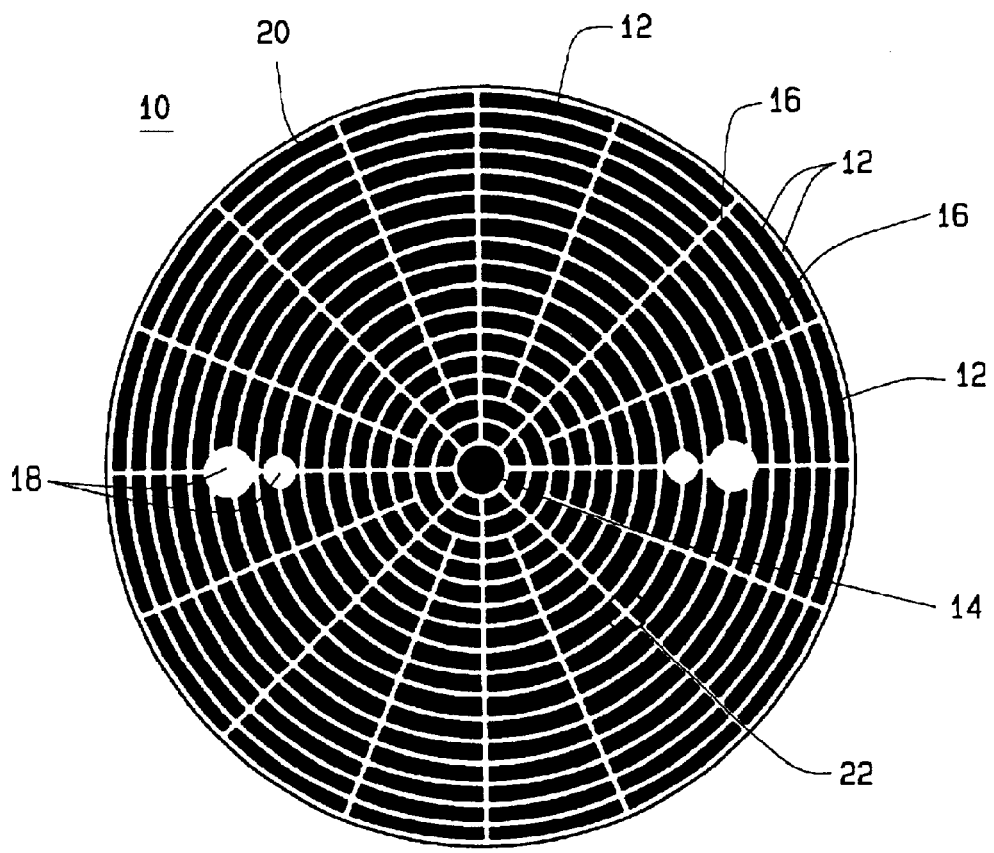
FIG. 1 is a flattened front view of a pattern to be illuminated on a screen according the present invention.

A placido pattern 10 for use in obtaining a topographic image of an eye is shown in FIG. 1. The pattern 10 includes a series of spaced arcuate segments 12 centered about a central point 14 and a series of spaced radial lines 16 emanating from the central point 14. Each pair of adjacent radial lines 16 can be said to define a boundary of a portion of the arcuate segments 12. Placido pattern 10 also preferably includes holes or apertures 18 for allowing illumination devices and cameras (not shown) to obtain images of an eye being measured. Central portion or points 14 may be light or dark compared to segments 12 and lines 16 depending on the method of object illumination.

Preferably, each of the arcuate segments 12 and radial lines 16 are light colored relative to the other areas 20 of the placido pattern. This prevents the lighter portion of the images from overpowering the dark portions when being viewed by an image capture device. If the lines were darker colored, the lighter colored blocks could lighten the overall image, causing loss of detail in the thin darker areas and loss of dynamic range of the image. Also, preferably each of the arcuate segments and radial lines are evenly spaced with respect to the other arcuate segments 12 and radial lines 16 of the pattern 10 as shown in FIG. 1. In addition, the placido pattern 10 is preferably disposed on a single curvature placido plate, such as described in U.S. Pat. No. 5,864,383 to Turner, et al. entitled "Single-Curvature Placido Plate", which is herein incorporated by reference in its entirety.

Another way of describing placido pattern 10 would be as a series of spaced concentric rings centered about a central point 14 and a series of spaced radial lines emanating from the central point 14. In this manner, arcuate segments 12 would become concentric rings with the rings forming a complete circle about the central point 14, such that a plurality of wedge-shapes are formed with a plurality of spaced arcuate segments 12 within each wedge-shape, wherein each wedge-shape is defined by adjacent radial lines 16.

Still another way of describing pattern 10, is that it consists of a series of spaced concentric rings centered about a central point 14 and a series of spaced radial spoke-like lines 16 emanating from the central point 14, such that the rings and lines form a spider-web-like pattern.

The placido pattern 10 of FIG. 1 differs from the prior art in that the novel pattern 10 is a combination of dark colored blocks 20 separated by a light colored grid formed by lines 16 and arcuate segments 12 in a circular pattern. The grid is a series of lines that appear to be emanating from the center 14 of the image as a converging point and radiating away from that center point 14 as evenly spaced angles such as spokes of a wheel. The grid then has additional circular rings attached to the radial pattern. The concentric rings are also centered around the center 14 of the array. The circles are regularly spaced such that each series of concentric dark blocks appear to be equal in both length and height.

Preferably, the lines 16 and arcuate segments 12 are sized to be easily viewed with imaging optics and a capture device such as a CCD camera. If the lines 16 and segments 12 are too thin, the lines may be difficult for the sensing devices to resolve. This difficulty makes the edges of the dark blocks 20 appear to be dim and difficult for the camera and software algorithms to differentiate from surrounding information. Preferably, the arcuate segments 12 and lines 16 should be at least 3 pixels wide. The advantage of capturing the images of the segments 12 and lines 16 based upon adequately wide images, is that the captured images are more clear and the signal generated by the captured device is better than with lines that are too closely spaced. The image resolution can best be understood in the context of understanding that the captured images are resolved into pixels on a sensor surface. If the magnified captured image of the width of a grid line is less than 2 pixels, it is difficult to determine the edge location of lines or segments, and difficult to find the corners of blocks 20.

Figure 2:
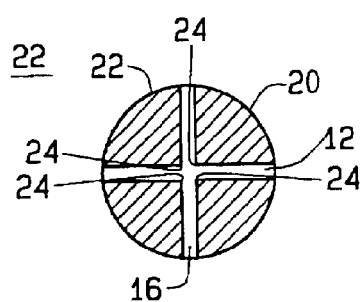
FIG. 2 is an enlarged portion of FIG. 1.
Figure 3:
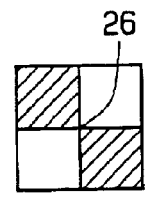
FIG. 3 is a portion of a prior art pattern.

FIG. 2 illustrates the advantage of the present invention over the prior art of FIG. 3. FIG. 2 is a magnified portion 22 of pattern 10. The intersection of arch 12 and line 16 presents four data points 24 within a relatively small cross-section of area as compared to the single data point 26 obtained at the intersection of light and dark squares of the prior art of FIG. 3.

The checkered grid pattern of FIG. 3 only has available points along the edges of each block and the intersection corners of each block which is where ways for determining twist angle error are defined. The separation of blocks 20 by white grid lines (formed by arcuate segments 12 and radial lines 16) is beneficial due to the fact that each intersection point takes one place of intersection and creates four distinct data points which are easy to locate and calculate. So, in addition to the normal twist angle points, there are four twist angle data points located in close proximity to each other in addition to the edges of each block 20 that may be used for calculation of angle change. The proximity of the edges and width change of the blocks provides much more information with which to calculate anterior surface elevation of a cornea than with the prior art checkered pattern of FIG. 3.

In U.S. Pat. No. 5,864,383, the image shown in FIG. 10 demonstrates a simple raster grid pattern. The advantage of the new design over the previous art is that it is easier to properly center and register the image to the cornea of the eye. The present design, consisting of radial lines and circular segments, promotes the cent ration of the eye, and allows for a better systematic review of each vertex with each possible ray location on the image using a more traditional approach to image review and analysis. In addition, the absence of image information at each vertex caused by the line spacing, allows 4 vertex points to be used compared to 1 if the segment vertices meet at each corner. Additionally as discussed before, the equally square segments when reflected off of a cornea, are not regular polygons in the image and are more difficult to systematically review.

Figure 4:
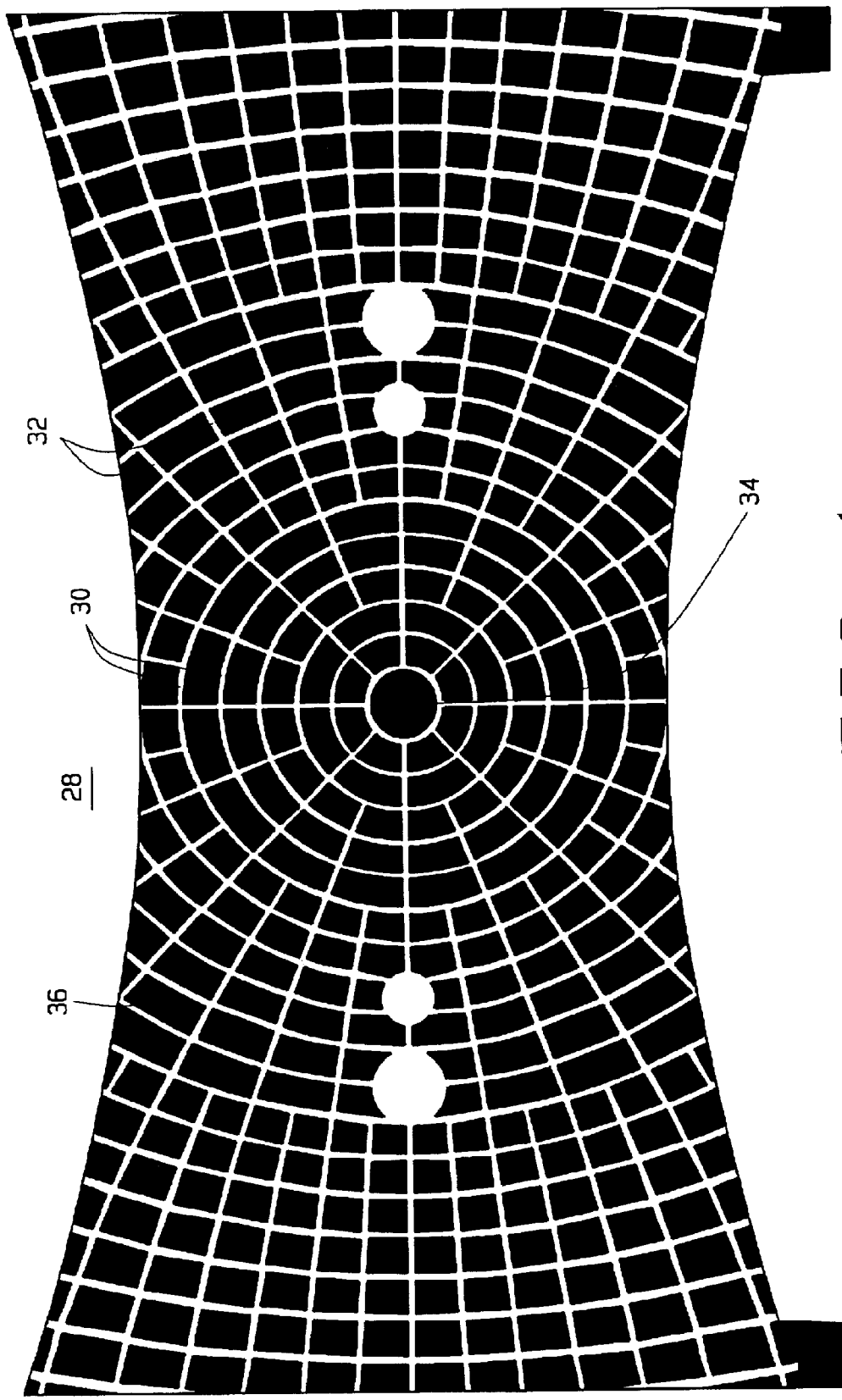
FIG. 4 is a flattened front view of an alternate pattern to be illuminated on a screen according to the present invention.

FIG. 4 discloses a placido pattern 28 which is similar to pattern 10 in that it has a series of concentric rings 30 and radial lines 32. One of the main differences between pattern 28 and pattern 10 is that the radial lines 32 begin at various distances from center point 34 and hence, create dark blocks 36 of varying sizes. This helps to prevent the image from having very small sections with which to calculate and also aids in the systematic location of the vertices and edges and associated rays for each segment of the image.

Figure 5:
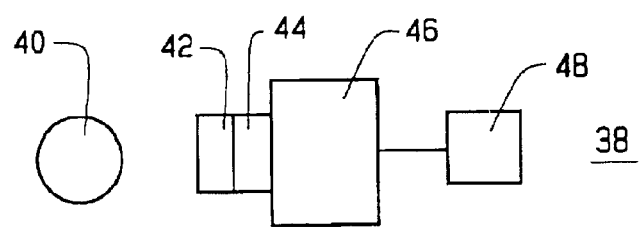
FIG. 5 is a block diagram of a corneal topography system in accordance with the present invention.

FIG. 5 discloses a block diagram of a system 38 for measuring a topography of an eye 40. The system 38 includes a placido plate 42 having a placido pattern in accordance with the present invention, a light source 44 for projecting the placido pattern onto the cornea 40. The placido image is captured by the topography instrument 46 and displayed on display 48. Preferably, the topography instrument is an Orbscan™ device available from Bausch & Lomb Incorporated or other known corneal topography device.

Thus, there has been described a placido pattern for use in obtaining a topography of an eye.

We claim:

1. A placido pattern for use in obtaining a topography of an eye comprising:

a series of spaced arcuate segments centered about a central point;

a series of spaced radial lines emanating from the central point, such that each pair of adjacent radial lines defines a boundary of a portion of the arcuate segments; and wherein the arcuate segments and radial lines combine to form a plurality of blocks, such that a spider-web-like pattern is formed and the blocks are a contrasting color relative to the arcuate segments and radial lines.

2. The placido pattern of claim 1 wherein each of the arcuate segments and radial lines are light colored relative to other areas of the placido pattern.

3. The placido pattern of claim 1 wherein each of the arcuate segments and radial lines are evenly spaced with respect to other arcuate segments and radial lines of the pattern.

4. The placido pattern of claim 1 wherein the pattern is disposed on a single-curvature plate.

5. The placido pattern of claim 1 wherein the arcuate segments and radial lines in the image are at least 3 pixels wide.

* * * * *